United States Patent
Plos et al.

(10) Patent No.: US 7,179,306 B2
(45) Date of Patent: Feb. 20, 2007

(54) PROCESS FOR DYING KERATIN FIBERS COMPRISING AT LEAST ONE ARYL OR ARYLOXY SUBSTITUTENT-BASED NINHYDRIN DERIVATIVE

(75) Inventors: Grégory Plos, Tokyo (JP); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 385 days.

(21) Appl. No.: 10/898,370

(22) Filed: Jul. 26, 2004

(65) Prior Publication Data

US 2005/0050655 A1 Mar. 10, 2005

Related U.S. Application Data

(60) Provisional application No. 60/499,507, filed on Sep. 3, 2003.

(30) Foreign Application Priority Data

Jul. 25, 2003 (FR) .................................. 03 09171
Mar. 4, 2004 (FR) .................................. 04 02247

(51) Int. Cl.
*A61K 7/13* (2006.01)
(52) U.S. Cl. ...................... 8/405; 8/406; 8/407; 8/410; 8/411; 8/421; 8/437; 8/607; 568/327
(58) Field of Classification Search ............... 8/405, 8/406, 407, 410, 411, 421, 437, 607; 568/327
See application file for complete search history.

(56) References Cited

FOREIGN PATENT DOCUMENTS

| DE | 43 17 855 | 12/1994 |
|----|-----------|---------|
| DE | 4317855 A1 * | 12/1994 |
| DE | 43 35 627 | 4/1995 |
| DE | 197 17 222 | 10/1998 |
| DE | 197 45 355 | 4/1999 |
| DE | 198 45 481 | 4/2000 |

OTHER PUBLICATIONS

English Abstract of the Patent No. DE 4317855 A1.*
STIC Search Report (Aug. 7, 2006).*

Della et al. "Synthesis of Fingerprint Reagents: Aromatic Nucleophilic Substitution as a Route to 5-Substituted Ninhydrin," Synthesis, No. 12, 2119-2123, 1999.

Hauze et al., "New Reagents for the Development of Fingerprints," Proceedings of the International Symposium on Fingerprint Detection and Identification, Jun. 26-30, 1995, Ne'urim, Israel, 119-122.

Hark et al. "Novel Approaches toward Ninhydrin Analogs," Tetrahedron Lett., vol. 35, No. 42, 7719-7722, 1994.

Hark et al. "Synthesis of Aryl-Substituted Ninhydrin Analogs," Abstracts of Papers, part 1, 204th National Meeting of the American Chemical Society, Washington, DC, Aug. 23-28, 1992, ANYL 055.

Kametani et al, "Studies on the Synthesis of Heterocyclic Compounds, Part CDLIII Total Synthesis (±-)-Ochrobirine," J. Chem. Soc., Perkins Trans. I, 391-393, 1972.

Kobus et al., "Fingerprint Research in South Australia," Proceedings of the International Symposium on Fingerprint Detection and Identification, Jun. 26-30, 1995, Ne'urim, Israel, 227-230.

Lennard et al., "Synthesis of Ninhydrin Analogues and Their Application to Fingerprint Development: Preliminary results," J. Forens. Sci, Soc,. 1986, 26, 323-328.

Nalliah et al., "The Total Synthesis of (±) Ochrobirine," Canadian Journal of Chemistry, vol. 50, No. 12, 1819-1827, 1972.

Ruhemann, S., "Triketohydrindene Hydrate," J. Chem. Soc., 97, 2025-2031, 1910.

English language Derwent Abstract of DE 43 17 855, Dec. 1, 1994.
English language Derwent Abstract of DE 43 35 627, Apr. 20, 1995.
English language Derwent Abstract of DE 197 45 355, Apr. 15, 1999.

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

The present disclosure relates to the process, for dyeing keratin materials, comprising applying to the fibers a composition comprising, in a medium appropriate for dyeing, at least one ninhydrin derivative, which may optionally be combined with at least one compound comprising a labile hydrogen. Further disclosed herein is a multi-component hair dye composition, and a multi-compartment kit comprising same.

23 Claims, No Drawings

PROCESS FOR DYING KERATIN FIBERS COMPRISING AT LEAST ONE ARYL OR ARYLOXY SUBSTITUTENT-BASED NINHYDRIN DERIVATIVE

This application claims benefit of U.S. Provisional Application No. 60/499,507, filed Sep. 3, 2003.

The present disclosure relates to compositions for dyeing keratin materials, such as compositions for hair dyeing, comprising at least one ninhydrin derivative which in some embodiments is combined with at least one compound comprising a primary or secondary amine functional group or with at least one compound comprising an activated methylene functional group. Further disclosed herein is a method for dyeing using such compositions, and a multi-component dyeing kit used for carrying out such a method.

Throughout the years, people have sought to modify the color of their skin, of their eyelashes or of their hair, for instance to mask their grey hair. To do this, several technologies have been developed.

It is known to dye human keratin fibers, such as the hair, with dyeing compositions comprising oxidation dye precursors, generally called oxidation bases. These oxidation bases are colorless or slightly colored compounds which, when combined with oxidizing agents, give rise, through a process of oxidative condensation, to colored compounds. These dyes are insoluble and become trapped inside the hair fiber.

It is also known that it is possible to vary the shades obtained with oxidation bases by combining them with couplers or color modifiers. The variety of molecules used at the level of the oxidation bases and the couplers allows a rich palette of colors to be obtained.

The colors obtained can exhibit good longevity (also referred to as color-fastness) with exposure to shampoo. However, the oxidation reaction occurs with the aid of oxidizing products such as hydrogen peroxide in a basic medium. These oxidizing agents attack the keratin of the hair, which can cause the cosmetic and mechanical properties to deteriorate considerably in the event of repeated dyeing.

It is also known to dye human keratin fibers by direct dyeing, which comprises applying to keratin fibers direct dyes that are colored and dyeing molecules having affinity for the fibers. There may be mentioned, by way of examples of direct dyes which are conventionally used, nitro dyes, benzene dyes, anthraquinone dyes, nitropyridine dyes, azo dyes, cationic azo dyes, xanthene dyes, acridine dyes, azine dyes or dyes of the triarylmethane type or natural dyes.

The colors that can thus be obtained are quite chromatic and do not bring about chemical degradation of keratin, but have the disadvantage of being only temporary or semipermanent, that is to say the color can fade after only 4 to 5 shampooings.

A need therefore remains for systems and methods for dyeing which allow good color fastness to be obtained without involving the use of oxidizing agents which are likely to damage keratin materials.

Accordingly, the present diclosure relates to the use of ninhydrin derivatives described in greater detail below, which make it possible to dye keratin materials, such as the hair, with color fastness that can be equivalent or even superior to that obtained by oxidation dyeing, this being in the absence of strong oxidizing agents, thereby preserving the keratin materials.

The ninhydrin derivatives as disclosed herein may be used, for example, in combination with compounds comprising a labile hydrogen, such as primary or secondary amines or compounds comprising an activated methylene functional group.

The colors thus obtained can exhibit good chromaticity and are distinguishable for instance by excellent fastness to washing (several tens of shampooings).

An aspect of the present disclosure, therefore is the process for dyeing keratin materials, comprising applying to the keratin materials a composition comprising, in a medium appropriate for dyeing, at least one ninhydrin compound of formula (I):

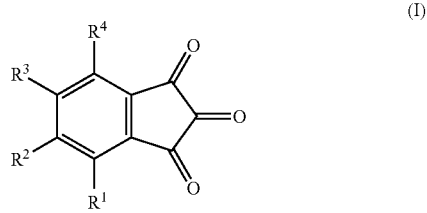

wherein:

$R^1$, $R^2$, $R^3$ and $R^4$, which may be identical or different, are chosen from hydrogen atoms; carboxy($C_{1-6}$ alkyl) radicals; ($C_{1-6}$ alkyl)carboxy($C_{1-6}$ alkyl) radicals; 6-membered aryloxy radicals; 5-membered heteroaryloxy radicals comprising at least one heteroatom chosen from N, O, S and P; aryl radicals comprising at least 5 members, which are monocyclic or polycyclic, fused or non-fused, optionally comprising at least one heteroatom chosen from N, O, S and P;

wherein the aryloxy, heteroaryloxy, aryl and heteroaryl radicals optionally bear at least one substituent chosen from halogens, $C_{1-9}$ alkyl radicals, hydroxyl radicals, $C_{1-6}$ alkoxy radicals, amino radicals, mono- and di($C_{1-6}$ alkyl)amino radicals, mono- and di($C_{1-6}$ hydroxyalkyl)amino radicals, thio radicals, $C_{1-6}$ alkylthio radicals, $C_{1-6}$ thioalkyl radicals, ($C_{1-6}$ alkyl)-carbonyl radicals, hydrogenocarbonyl radicals, hydroxycarbonyl radicals, ($C_{1-6}$ alkoxy)carbonyl radicals, nitro radicals, sulphonato radicals, tri($C_{1-6}$ alkyl)ammonio radicals, imidazolyl radicals, pyridinyl radicals, and the corresponding protonated groups, such as ammonio, imidazolio and pyridinio; and two adjacent substituents together are the group —O—$CH_2$—O—;

with the proviso that at least one of the radicals $R^1$, $R^2$, $R^3$, and $R^4$ is not a hydrogen atom, or $R^1$ and $R^2$, $R^2$ and $R^3$ or $R^3$ and $R^4$ together form the group —O—$CH_2$—O—.

Such compositions are, for instance, useful for dyeing keratin fibers, such as the hair.

The above ninhydrin derivatives of formula (I) are used according to the present disclosure in a cosmetically acceptable medium generally comprising a large fraction of water. When they are dissolved in such an aqueous medium, the ninhydrin derivatives of formula (I) are in hydration equilibrium with the geminal diol form (or carbonyl hydrate) of the following formula (I)a:

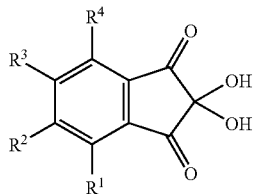
(I)a

When reference is made, in the present disclosure, to ninhydrin derivatives of formula (I), such references always include not only the compounds of formula (I) but also the corresponding hydrated forms of formula (I)a.

When the radicals $R^1$, $R^2$, $R^3$ and $R^4$ are chosen from aryl, heteroaryl, aryloxy and heteroaryloxy rings, the substituents of these rings may be chosen, for example, so that this ring forms, with the indan ring, a system of delocalized π electrons. Such systems can give colors which have beneficial chromaticities.

Non-limiting examples of ninhydrin derivatives that can be used in accordance with the present disclosure for dyeing hair fibers include the following:

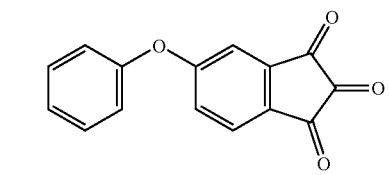
(a)

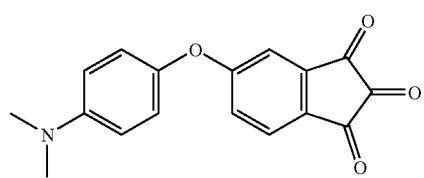
(b)

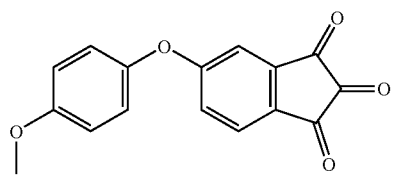
(c)

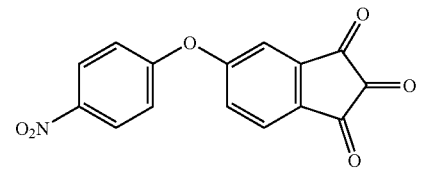
(d)

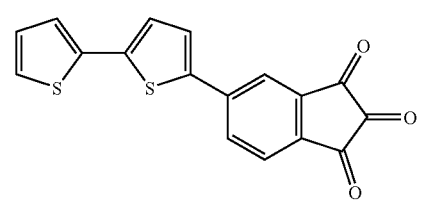
(e)

-continued

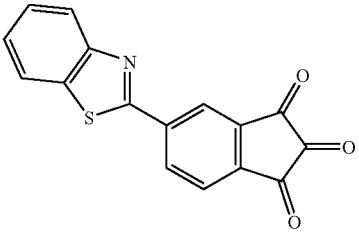
(f)

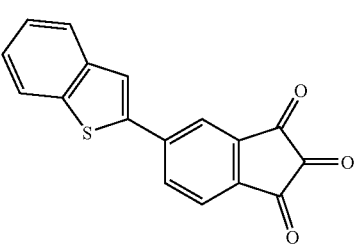
(g)

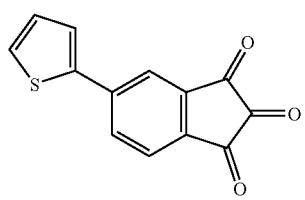
(h)

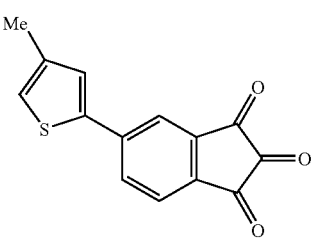
(i)

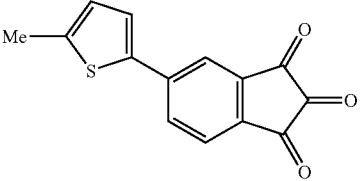
(j)

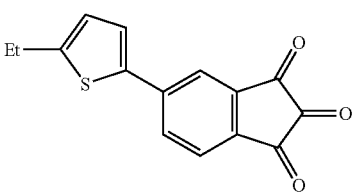
(k)

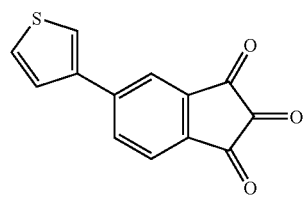
(l)

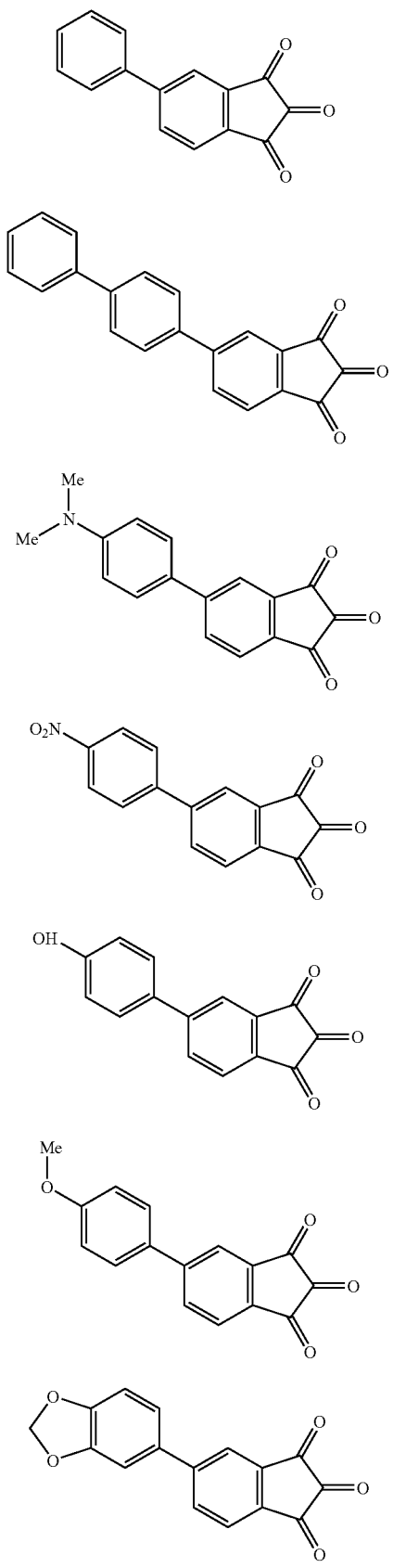
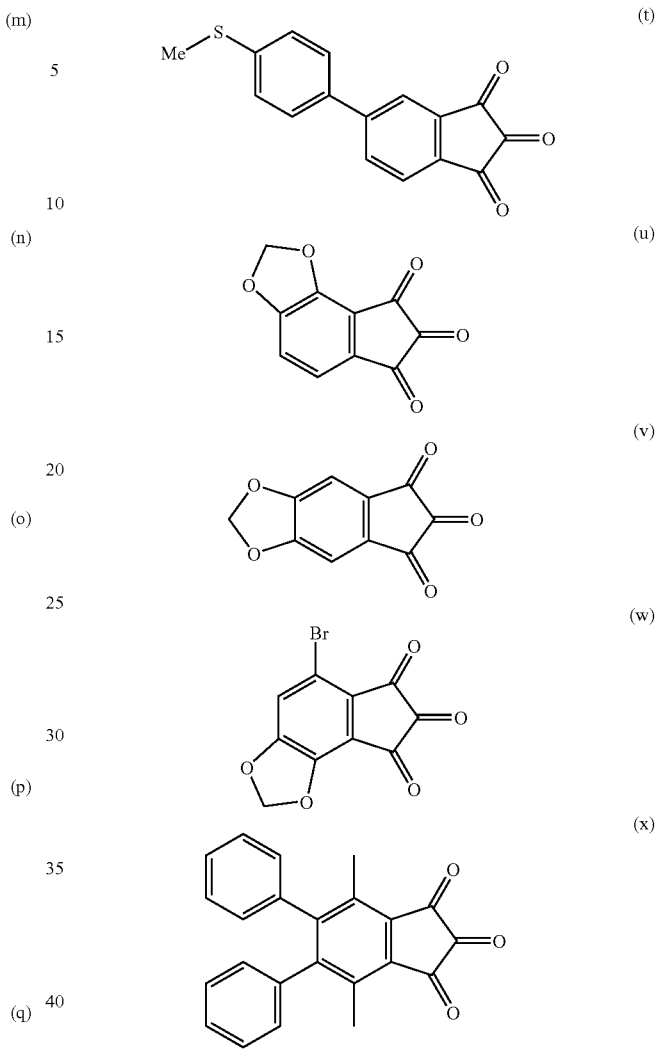

The ninhydrin derivatives used as disclosed herein are known. The synthesis of the above ninhydrin derivatives (a) to (x) is described in the following publications:

(a) Kobus H. J., Pigou P. E., Della E. W., Taylor B., Davies P. J., *Fingerprint Research in South Australia*, in Almog J., Springer E., ed. Proceedings of the International Symposium on Fingerprint Detection and Identification, Ne'urim, Israel: Hemed Press, 1995, 227–230;

(b) Kobus H. J., Pigou P. E., Della E. W., Taylor B., Davies P. J., *Fingerprint Research in South Australia*, in Almog J., Springer E., ed. Proceedings of the International Symposium on Fingerprint Detection and Identification, Ne'urim, Israel: Hemed Press, 1995, 227–230;

(c) Della E. W., Janowski W. K., Pigou P. P., Taylor B. M., *Synthesis of Fingerprint Reagents: Aromatic Nucleophilic Substitution as a Route to 5-substituted Ninhydrins, Synthesis*, 1999, 12, 2119–2123;

(d) 2,2-dihydroxy-5-(4-nitro-phenoxy)-indan-1,3-dione: Kobus H. J., Pigou P. E., Della E. W., Taylor B., Davies P. J., *Fingerprint Research in South Australia*, in Almog J., Springer E., ed. Proceedings of the International Symposium on Fingerprint Detection and Identification, Ne'urim, Israel: Hemed Press, 1995, 227–230;

(e) Hark R. R., Hauze D. B., Petrovskaïa O., Joullié M. M., Jahouari R., McComiskey P., *Novel Approaches toward Ninhydrin Analogs*, Tetrahedron Lett. 1994, 35, 7719–7722

(f) Hark R. R., Hauze D. B., Petrovskaïa O., Joullié M. M., Jahouari R., McComiskey P., *Novel Approaches toward Ninhydrin Analogs*, Tetrahedron Lett. 1994, 35, 7719–7722

(g) 5-benzo[b]thiophen-2-yl-2,2-dihydroxy-indan-1,3-dione: Hark R. R., Hauze D. B., Petrovskaïa O., Joullié M. M., Jahouari R., McComiskey P., *Novel Approaches toward Ninhydrin Analogs*, Tetrahedron Lett. 1994, 35, 7719–7722

(h) Hark R. R., Hauze D. B., Joullié M. M., *Synthesis of Aryl-Substituted Ninhydrin Analogs*, Abstracts of Papers, part 1, 204th National Meeting of the American Chemical Society, Washington, D.C., Aug. 23–28, 1992, Am. Chem. Society Washington D.C., 1992, ANYL 055

(i) Hark R. R., Hauze D. B., Petrovskaïa O., Joullié M. M., Jahouari R., McComiskey P., *Novel Approaches Toward Ninhydrin Analogs*, Tetrahedron Lett. 1994, 35, 7719–7722

(j) Hark R. R., Hauze D. B., Petrovskaïa O., Joullié M. M., Jahouari R., McComiskey P., *Novel Approaches toward Ninhydrin Analogs*, Tetrahedron Left. 1994, 35, 7719–7722

(k) Hark R. R., Hauze D. B., Petrovskaïa O., Joullié M. M., Jahouari R., McComiskey P., *Novel Approaches toward Ninhydrin Analogs*, Tetrahedron Left. 1994, 35, 7719–7722

(l) Hark R. R., Hauze D. B., Petrovskaïa O., Joullié M. M., Jahouari R., McComiskey P., *Novel Approaches toward Ninhydrin Analogs*, Tetrahedron Left. 1994, 35, 7719–7722

(m) Hark R. R., Hauze D. B., Joullié M. M., *Synthesis of Aryl-Substituted Ninhydrin Analogs*, Abstracts of Papers, part 1, 204th National Meeting of the American Chemical Society, Washington, D.C., Aug. 23–28,1992, Am. Chem. Society Washington D.C., 1992, ANYL 055

(n) Hark R. R., Hauze D. B., Joullié M. M., *Synthesis of Aryl-Substituted Ninhydrin Analogs*, Abstracts of Papers, part 1, 204th National Meeting of the American Chemical Society, Washington, D.C., Aug. 23–28,1992, Am. Chem. Society Washington D.C., 1992, ANYL 055

(o) Hark R. R., Hauze D. B., Petrovskaïa O., Joullié M. M., Jahouari R., McComiskey P., *Novel Approaches toward Ninhydrin Analogs*, Tetrahedron Left. 1994, 35, 7719–7722

(p) Kobus H. J., Pigou P. E., Della E. W., Taylor B., Davies P. J., *Fingerprint Research in South Australia*, in Almog J., Springer E., ed. Proceedings of the International Symposium on Fingerprint Detection and Identification, Ne'urim, Israel: Hemed Press, 1995, 227–230

(q) Hauze D. B., Petrovskaïa O., Joullié M. M., Hark R. R., *New Reagents for the Development of Fingerprint*, in Almog J., Springer E., ed. Proceedings of the International Symposium on Fingerprint Detection and Identification, Ne'urim, Israel: Hemed Press, 1995, 119–123

(r) Della E. W., Janowski W. K., Pigou, P. P., Taylor B. M., *Synthesis of Fingerprint Reagents, Aromatic Nucleophilic Substitution as a Route to 5-substituted Ninhydrins*, Synthesis, 1999, 12, 2119–2123

(s) Hark R. R., Hauze D. B., Joullié M. M., *Synthesis of Aryl-Substituted Ninhydrin Analogs*, Abstracts of Papers, part 1, 204th National Meeting of the American Chemical Society, Washington, D.C., Aug. 23–28, 1992, Am. Chem. Society Washington D.C., 1992, ANYL 055

(t) Della E. W., Janowski W. K., Pigou, P. P., Taylor B. M., *Synthesis of Fingerprint Reagents, Aromatic Nucleophilic Substitution as a Route to 5-substituted Ninhydrins*, Synthesis, 1999, 12, 2119–2123

(u) Kametani T., Hibino S., Takano S., *Studies on the Synthesis of Heterocyclic Compounds, part CDLIII Total Synthesis of (±)-ochrobirine*, J. Chem. Soc., Perkin Trans. 1, 1972, 391–393

(v) 6,6-dihydroxy-indeno[5,6-d][1,3]d ioxole-5,7-d ione: Ruhemann S., *Triketohydrindene Hydrate*, Trans. Chem. Soc. 1910, 97, 2025–2031

(w) Nalliah B., Ahmed Q. A., Manske R. H. F., *The Total Synthesis of (±)-ochrobirine*, Can. J. Chem., 1972, 50, 1819–1824

(x) Lennard C. J. Margot P. A. Stoilovic M., Warrener R. N. *Synthesis of Ninhydrin Analogues and Their Application to Fingerprint Development: Preliminary results*, J. Forens. Sci. Soc., 1986, 26, 323–328

In accordance with the present disclosure, the ninhydrin derivatives of formula (I) described above may be used alone for dyeing keratin materials. For example, these compounds are capable of generating colored molecules with the amine functional groups of keratin, i.e., a colored reaction.

It may also be possible to use the at least one compound of formula (I) together with at least one activator that makes it possible to modify the kinetics of reaction of the ninhydrin compound with the keratinous material. Such an activator may be an oxidizing agent, a reducing agent, Brönsted acids, a metal catalyst such as catalysts based on a transition metal such as iron, platinum and palladium, proteins, for instance, enzymes, compounds which modify the ionic strength of the medium, such as NaCl salts, compounds comprising a labile hydrogen chosen from those comprising primary or secondary amine functional groups and those comprising activated methylene functional groups. It is, of course, also possible to use a mixture of such compounds.

For example, the compounds with primary amine or secondary amine functional groups may be aromatic amines.

Non-limiting mention, may also be made, for example, of aromatic amines including, N,N-dimethyl-p-phenylenediamine, N,N-diethyl-p-phenylenediamine, N-(2-hydroxyethyl)-N-ethyl-p-phenylenediamine, N,N-bis-(2-hydroxyethyl)-p-phenylenediamine, N-(2-methoxyethyl)-p-phenylenediamine, 2,3-, 2,4- or 2,5-dichloro-p-phenylenediamine, 2-chloro-p-phenylenediamine, dibromohydrate of 2,5-dihydroxy-4-morpholinoaniline, 2-, 3- or 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)4-methoxy-2-methylphenol, 4-amino-2-hydroxymethylphenol, 1,3-diamino-2,4-dimethoxybenzene, 2-, 3-, 4-aminobenzoic acid, 2-amino-, 3-amino- or 4-aminophenylacetic acid, 2,3-, 2,4-, 2,5-, 3,4- or 3,5-diaminobenzoic acid, 4-amino- or 5-aminosalicylic acid, 3-amino-4-hydroxybenzoic acid, 4-amino-3-hydroxybenzoic acid, 2-amino-, 3-amino or 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraminobenzene, 2,4,5-triaminophenol, pentaminobenzene, hexaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising another aromatic residue, of formula (II)

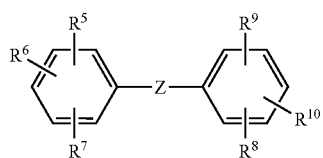

wherein:

$R^5$ is chosen from hydroxyl radicals and amino radicals optionally substituted with $C_{1-4}$ alkyl, $C_{1-4}$ hydroxyalkyl and $(C_{1-4}$ alkoxy$)$-$(C_{1-4}$ alkyl$)$radicals, $R^6$, $R^7$, $R^8$, $R^9$ and $R^{10}$, which may be identical or different, are chosen from hydrogen atoms, hydroxyl radicals, carboxylic acid radicals, sulphonic acid radicals, and amino radicals optionally substituted with an entity chosen from $C_{1-4}$ alkyl, $C_{1-4}$ hydroxyalkyl and $(C_{1-4}$ alkoxy$)$-$(C_{1-4}$ alkyl$)$ radicals, Z is chosen from a direct bond, $C_{1-4}$ hydrocarbon radicals which may be saturated or unsaturated, optionally hydroxylated, carbonyl, sulphonyl and imino radicals, oxygen and sulfur atoms, and groups of formula Q-$(CH_2$—P—$CH_2$-Q'$)_o$ wherein "$o$" is a number ranging from 1 to 4, P is chosen from a direct bond and —$CH_2$— and —CHOH— radicals, Q and Q', which may be identical or different, are chosen from oxygen atoms, $NR^{11}$ radicals wherein $R^{11}$ is chosen from a hydrogen atom, and $C_{1-4}$ alkyl, $C_{1-4}$ hydroxyalkyl, O—$(CH_2)_p$NH and NH—$(CH_2)_{p'}$—O radicals, wherein p and p' are chosen from 2 or 3.

The nonaromatic primary or secondary amines may be chosen from, for example, 2-aminoethanol, 2-methoxyethylamine, 2-ethoxyethylamine, 2-(2-aminoethoxy)ethanol, 2- or 3-aminopropanol, 2,3-dihydroxypropylamine, 4-hydroxypropylamine, 2-aminopropane-1,3-diol, 2-amino-2-methylpropanol, 2-amino-2-methyl propane-1,3-diol, 2-amino-2-hydroxymethyl propane-1,3-diol, tetrahydropentylamine, pentahydroxyhexylamines such as glucamine, D-glucosamine, D-galactosamine, 1,2-diaminoethane, 1,2- or 1,3-diaminopropane, 1,3-diamino-2-propanol, 2-(2-aminoethylamino)ethylamine, 2-(2-aminoethylamino)ethanol, 3-(2-aminoethylamino)propylamine and 3-(2-aminoethylamino) propanol.

The compounds comprising an activated methylene functional group may be chosen, for example, from 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone and 1-methyl-3-phenyl-2-pyrazolinone.

Some primary and secondary amines, and some compounds comprising activated methylene functional groups, and other compounds comprising a labile hydrogen are also described in the German Patent Application Nos. DE 43 17 855, DE 197 17 222, DE 198 45 481 and DE 197 45 355, where they are used for dyeing keratin fibers in combination with compounds different from the ninhydrin derivatives of formula (I).

When the ninhydrin derivatives of formula (I) are used in combination with a primary or secondary amine or with a compound comprising an activated methylene functional group, it is necessary to store these different reagents separately in order to avoid a premature color reaction. The reagents are then only brought into contact immediately before application to the hair by freshly mixing two compositions comprising the ninhydrin derivatives and the primary or secondary amine and/or the compound comprising an activated methylene functional group, respectively.

Another aspect of the present disclosure is a multicomponent ready-to-use dyeing composition comprising
  at least one first component comprising a composition comprising at least one ninhydrin derivative of formula (I), and
  at least one second component comprising a composition comprising at least one entity chosen from compounds comprising primary and secondary amine radicals, and compounds comprising an activated methylene functional group, as described above.

This multicomponent ready-to-use dyeing composition may be provided, for example, in the form of a multicompartment kit, with at least one first compartment comprising the at least one first component, and at least one second compartment comprising the at least one second component.

Yet another aspect of the present disclosure is a cosmetic dyeing composition comprising at least one ninhydrin derivative of formula (I) and at least one cosmetic active ingredient.

The cosmetic active ingredients that may be present in the cosmetic compositions of the present disclosure are chosen, for example, from vitamins, saccharides, oligosaccharides, polysaccharides which are optionally hydrolyzed and optionally modified, amino acids, oligopeptides, peptides, proteins which are optionally hydrolyzed and optionally modified, polyamino acids, enzymes, fatty acids and alcohols that are optionally branched, animal, vegetable and mineral waxes, ceramides and pseudoceramides, hydroxylated organic acids, UV-screening agents, antioxidants and anti-free-radical agents, chelating agents, antidandruff agents, seborrhoea-regulating agents, soothing agents, cationic, anionic, nonionic and amphoteric surfactants, cationic, anionic, neutral and amphoteric polymers, silicones that are optionally organomodified, mineral, vegetable and animal oils, polyisobutenes and poly(α-olefins), fatty esters, anionic polymers in dissolved or dispersed form, nonionic polymers in dissolved or dispersed form, reducing agents, hair dyes such as direct dyes and oxidation dye precursors (bases and/or couplers) different from the claimed compounds comprising primary and secondary amine functional groups, oxidants such as hydrogen peroxide optionally combined with persalts, pigments and mixtures thereof.

The at least one cosmetic active ingredient, when present, may, for example, be present in an amount ranging from 0.001 to 50% by weight, for instance, from 0.01 to 20% by weight, such as in an amount ranging from 0.1 to 10% by weight, relative to the total weight of the cosmetic composition.

In one embodiment of the cosmetic dyeing composition according to the present disclosure, the cosmetic additive ingredient is at least one ingredient chosen from surfactants and/or a polymeric agents (polymers), it being possible for these agents to be of a nonionic, cationic, anionic or amphoteric nature.

As disclosed herein, the hair dyeing compositions used according to the present disclosure are stable during storage when they comprise, as sole reagents, at least one ninhydrin derivative of formula (I), but the compositions must be prepared immediately before use when they comprise both at least one ninhydrin derivative of formula (I) and at least one compound comprising a labile hydrogen, such as primary and secondary amines, or compounds comprising an activated methylene functional group.

These ready-to-use dyeing compositions, whether they are stable during storage or prepared immediately before use, may have a pH, for example, ranging from 2 to 12, for instance, from 3 to 11.

The at least one ninhydrin derivative of formula (I) may be, for example, present in an amount ranging from 0.0001% to 30% by weight, relative to the total weight of the composition.

The compounds comprising a labile hydrogen which are used in combination with the at least one ninhydrin derivative of formula (I), may be present, for instance, in an amount ranging from 0.0001 to 30% by weight, relative to the total weight of the composition.

Still another aspect of the present disclosure is a process for hair dyeing comprising the application, to the hair, of a ready-to-use hair dyeing composition as described above. This composition is left in contact with the hair fibers for a time sufficient to obtain the desired color. This leave-in time can range from 5 minutes to 1 hour, such as from 15 to 30 minutes. The colored reaction between the at least one ninhydrin derivative and the amine functional groups of the keratin or the compounds comprising a labile hydrogen which may be present, may be accelerated by heating hair impregnated with the dyeing composition. The heating temperature can be less than or equal to 80° C., such as less than or equal to 60° C.

After obtaining the desired color, the hair is rinsed and washed.

When compounds comprising a labile hydrogen such as primary or secondary amines, or compounds comprising an activated methylene functional group are used, the application of the reagents taking part in the colored reaction may also be performed in two stages. In other words, it is possible to successively apply two different compositions respectively comprising at least one ninhydrin derivative of formula (I), and at least one compound comprising a primary or secondary amine functional group, or an activated methylene functional group.

Still another aspect of the present disclosure is a two-stage dyeing process comprising the application, to the hair, one after the other, in any order, of a composition comprising at least one ninhydrin derivative of formula (I), and a composition comprising at least one compound comprising a primary or secondary amine functional group, or an activated methylene functional group as defined above for the multicomponent ready-to-use dyeing agent.

This separate application of the two reactive compositions has the advantage of avoiding the handling of colored compositions and thus reduces the risks of staining materials such as clothes.

Satisfactory hair colors are also obtained when an intermediate rinsing stage is inserted between the application of the first composition and the application of the second composition.

In a similar manner to that described above, hair impregnated with either one of the two compositions of the multicomponent dyeing process may be heated, for example, to a temperature of less than or equal to 80° C., such as to a temperature less than or equal to 60° C., such heating making it possible to accelerate the colored reaction and to shorten the leave-in time.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The following example is intended to illustrate the invention in a non-limiting manner.

EXAMPLE

The following composition was prepared:

| | |
|---|---|
| 5-benzo[b]thiophene-2-yl-2,2-dihydroxyindan-1,3-dione (hydrate of the compound of formula (g)) | $10^{-2}$ moles |
| Ethanol | 50 g |
| NaOH | qs pH 7 |
| Distilled water | qs 100 g |

The composition was applied to two locks of hair, one natural, and one permanently waved, which were 90% white, of 1 g each. The bath ratio was 5, the leave-in time was 30 minutes and the temperature was 60° C. At the end of the leave-in time, the locks were rinsed and then washed with a standard shampoo.

The color intensity was evaluated by colorimetry according to the CIELAB system using a Minolta CM3600d colorimeter (illuminant D65, angle of observation: 10°, specular component included).

The CIELAB scoring system defines a colorimetric space in which each color is defined by three parameters (L*, a* and b*):

the parameter L* reflects the clarity of the color, the value of L* being equal to 0 for black and equal to 1 for absolute white; thus the higher the value of L*, the less intense the color, the parameter a* corresponds to the axis of the green-red antagonist pair and the parameter b* to the axis of the blue-yellow antagonist pair.

The table below shows the parameters L*, a* and b* of the locks of natural hair and of the permanently waved hair before and after the increase in the color, as ΔE defined by the equation below:

$$\Delta E = \sqrt{(L^*_{final} - L^*_{initial})^2 + (a^*_{final} - a^*_{initial})^2 + (b^*_{final} - b^*_{initial})^2}$$

ΔE reflects the overall variation in color. The higher the variation in color, the higher its value.

| Hair | | L* | a* | b* | ΔE | Color |
|---|---|---|---|---|---|---|
| Natural | Before dyeing | 60.84 | 0.03 | 11.63 | — | — |
| Natural | After dyeing | 52.87 | −2.73 | 15.29 | 10.07 | green |
| Permanently waved | Before dyeing | 61.78 | 0.33 | 12.74 | — | — |
| Permanently waved | After dyeing | 50.90 | −6.58 | 17.31 | 13.77 | green |

What is claimed is:

1. A process for dyeing keratin materials, comprising applying to the keratin materials a composition comprising, in a medium appropriate for dyeing, at least one ninhydrin compound of formula (I):

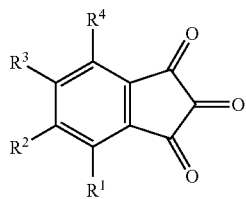

wherein $R^1$, $R^2$, $R^3$ and $R^4$, which may be identical or different, are chosen from hydrogen atoms; carboxy($C_{1-6}$ alkyl)radicals; ($C_{1-6}$ alkyl)carboxy($C_{1-6}$ alkyl) radicals; 6-membered aryloxy radicals; 5-membered heteroaryloxy radicals comprising at least one heteroatom chosen from N, O, S and P; aryl radicals comprising at least 5 members, which may be monocyclic or polycyclic, fused or non-fused, optionally comprising at least one heteroatom chosen from N, O, S and P;

wherein the aryloxy, heteroaryloxy, aryl and heteroaryl groups optionally bear at least one substituent chosen from halogen atoms, $C_{1-9}$ alkyl radicals, hydroxyl radicals, $C_{1-6}$ alkoxy radicals, amino radicals, mono- and di($C_{1-6}$ alkyl)amino radicals, mono- and di($C_{1-6}$ hydroxyalkyl)amino radicals, thio radicals, $C_{1-6}$ alkylthio radicals, $C_{1-6}$ thioalkyl radicals, ($C_{1-6}$ alkyl)carbonyl radicals, hydrogenocarbonyl radicals, hydroxycarbonyl radicals, ($C_{1-6}$ alkoxy)carbonyl radicals, nitro radicals, sulphonato radicals, tri($C_{1-6}$ alkyl)ammonio radicals, imidazolyl radicals, pyridinyl radicals, and the corresponding protonated radicals;

and two adjacent substituents may together comprise the group —O—CH$_2$—O—;

with the proviso that at least one of the radicals $R^1$, $R^2$, $R^3$, and $R^4$ is not a hydrogen atom, or $R^1$ and $R^2$, $R^2$ and $R^3$ or $R^3$ and $R^4$ are together form the group —O—CH$_2$—O—.

2. The process according to claim 1, wherein the corresponding protonated radcials are chosen from ammonio, imidazolio and pyridinio radicals.

3. The process according to claim 1, wherein when $R^1$, $R^2$, $R^3$ or $R^4$ is chosen from aryloxy, heteroaryloxy, aryl and heteroaryl radicals, at least one of the radicals chosen from $R^1$, $R^2$, $R^3$ and $R^4$ forms, with the indan ring, a system of delocalized π electrons.

4. The process according to claim 1, wherein the composition further comprises at least one activator that makes it possible to modify the kinetics of the reaction of the at least one ninhydrin compound of formula (I) with the keratin material.

5. The process according to claim 4, wherein the at least one activator is chosen from oxidizing agents, reducing agents, Brönsted acids, metal catalysts, proteins, compounds that modify the ionic strength of the medium, and compounds comprising a labile hydrogen chosen from compounds comprising a primary or secondary amine functional group and compounds comprising an activated methylene functional group.

6. The process according to claim 5, wherein the at least one compound comprising a primary or secondary amine functional group is an aromatic amine chosen from N,N-dimethyl-p-phenylenediamine, N,N-diethyl-p-phenylenediamine, N-(2-hydroxyethyl)-N-ethyl-p-phenylenediamine, N,N-bis-(2-hydroxyethyl)-p-phenylenediamine, N-(2-methoxyethyl)-p-phenylenediamine, 2,3-, 2,4- and 2,5-dichloro-p-phenylenediamine, 2-chloro-p-phenylenediamine, dibromohydrate of 2,5-dihydroxy-4-morpholinoaniline, 2-, 3- and 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)4-methoxy-2-methylphenol, 4-amino-2-hydroxymethylphenol, 1,3-diamino-2,4-dimethoxybenzene, 2-, 3-, 4-aminobenzoic acid, 2-amino-, 3-amino- and 4-aminophenylacetic acid, 2,3-, 2,4-, 2,5-, 3,4- and 3,5-diaminobenzoic acid, 4-amino- and 5-aminosalicylic acid, 3-amino-4-hydroxybenzoic acid, 4-amino-3-hydroxybenzoic acid, 2-amino-, 3-amino and 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2, 7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraminobenzene, 2,4,5-triaminophenol, pentaminobenzene, hexaminobenzene, 2,4,6-triaminoresorcinol, 4,5-diaminopyrocatechol, 4,6-diaminopyrogallol, 3,5-diamino- 4-hydroxypyrocatechol, and aromatic anilines and aromatic phenols comprising another aromatic residue of formula (II):

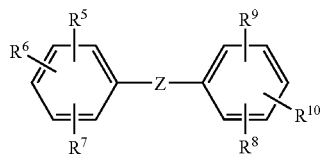

wherein:
  $R^5$ is chosen from hydroxyl and amino radicals optionally substituted with a radical chosen from $C_{1-4}$ alkyl, $C_{1-4}$ hydroxyalkyl and ($C_{1-4}$ alkoxy)-($C_{1-4}$ alkyl) radicals,
  $R^6$, $R^7$, $R^8$, $R^9$ and $R^{10}$, which may be identical or different, are chosen from hydrogen atoms, hydroxyl radicals, amino radicals optionally substituted with a radical chosen from $C_{1-4}$ alkyl, $C_{1-4}$ hydroxyalkyl, ($C_{1-4}$ alkoxy)-($C_{1-4}$ alkyl), carboxylic acid and sulphonic acid radicals,
  Z is chosen from a direct bond, $C_{1-4}$ hydrocarbon radicals that may be saturated or unsaturated and optionally hydroxylated, carbonyl, sulphonyl and imino radicals, oxygen and sulphur atoms, and radicals of formula Q-($CH_2$—P—$CH_2$-Q')$_o$ wherein "$o$" is a number ranging from 1 to 4, P is chosen from a direct bond, and —$CH_2$— and —CHOH— radicals, Q and Q', which may be identical or different, are chosen from oxygen atoms, $NR^{11}$ radicals wherein $R^{11}$ is chosen from a hydrogen atom, $C_{1-4}$ alkyl and $C_{1-4}$ hydroxyalkyl radicals, and O—($CH_2$)$_p$NH and NH—($CH_2$)$_{p'}$—O radicals wherein p and p' are equal to 2 or 3.

7. The process according to claim 5, wherein the at least one compound comprising a primary or secondary amine functional group is an aliphatic amine chosen from 2-aminoethanol, 2-methoxyethylamine, 2-ethoxyethylamine, 2-(2-aminoethoxy)ethanol, 2- and 3-aminopropanol, 2,3-dihydroxypropylamine, 4-hydroxypropylamine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines, glucamine, D-glucosamine, D-galactosamine, 1,2-diaminoethane, 1,2- and 1,3-diaminopropane, 1,3-diamino-2-propanol, 2-(2-aminoethylamino)ethylamine, 2-(2-aminoethylamino)ethanol, 3-(2-aminoethylamino)propylamine and 3-(2-aminoethylamino)propanol.

8. The process according to claim 5, wherein the compound comprising an activated methylene functional group is chosen from 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone and 1-methyl-3-phenyl-2-pyrazinone.

9. The process according to claim 1, wherein the composition has a pH ranging from 2 to 12.

10. The process according to claim 1, wherein the composition has a pH ranging from 3 to 11.

11. The process according to claim 1, wherein the at least one ninhydrin compound of formula (I) is present in an amount ranging from 0.0001% to 30% by weight, relative to the total weight of the composition.

12. The process according to claim 1, where in the composition further comprises at least one surfactant and/or a polymeric agent of nonionic, cationic, anionic or amphoteric nature.

13. A cosmetic composition for dyeing keratin fibers comprising, in a cosmetically acceptable medium, at least one surfactant and/or a polymeric agent of nonionic, cationic, anionic or amphoteric nature, and
  at least one ninhydrin compound of formula (I):

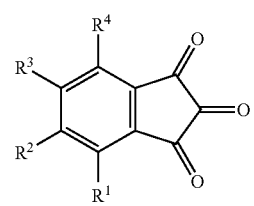

wherein
  $R^1$, $R^2$, $R^3$ and $R^4$, which may be identical or different, are chosen from hydrogen atoms; carboxy($C_{1-6}$ alkyl)radicals; ($C_{1-6}$ alkyl)carboxy($C_{1-6}$ alkyl) radicals; 6-membered aryloxy radicals; 5-membered heteroaryloxy radicals comprising at least one heteroatom chosen from N, O, S and P; aryl radicals comprising at least 5 members, which may be monocyclic or polycyclic, fused or non-fused, optionally comprising at least one heteroatom chosen from N, O, S and P; wherein the aryloxy, heteroaryloxy, aryl and heteroaryl groups optionally bear at least one substituent chosen from halogen atoms, $C_{1-9}$ alkyl radicals, hydroxyl radicals, $C_{1-6}$ alkoxy radicals, amino radicals, mono- and di($C_{1-6}$ alkyl)amino radicals, mono- and di($C_{1-6}$ hydroxyalkyl) amino radicals, thio radicals, $C_{1-6}$ alkylthio radicals, $C_{1-6}$ thioalkyl radicals, ($C_{1-6}$ alkyl)carbonyl radicals, hydrogenocarbonyl radicals, hydroxycarbonyl radicals, ($C_{1-6}$ alkoxy)carbonyl radicals, nitro radicals, sulphonato radicals, tri($C_{1-6}$ alkyl)ammonio radicals, imidazolyl radicals, pyridinyl radicals, and the corresponding protonated radicals;
and two adjacent substituents may together comprise the group —O—$CH_2$—O—;
  with the proviso that at least one of the radicals $R^1$, $R^2$, $R^3$, and $R^4$ are not a hydrogen atom,
  or $R^1$ and $R^2$, $R^2$ and $R^3$ or $R^3$ and $R^4$ are together form the group —O—$CH_2$—O—.

14. A ready-to-use cosmetic dyeing composition comprising, in a cosmetically acceptable medium,
  at least one ninhydrin compound of formula (I)

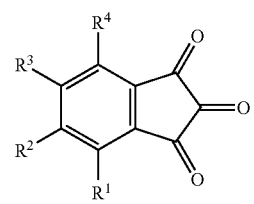

wherein

R$^1$, R$^2$, R$^3$ and R$^4$, which may be identical or different, are chosen from hydrogen atoms; carboxy(C$_{1-6}$ alkyl)radicals; (C$_{1-6}$ alkyl)carboxy(C$_{1-6}$ alkyl) radicals; 6-membered aryloxy radicals; 5-membered heteroaryloxy radicals comprising at least one heteroatom chosen from N, O, S and P; aryl radicals comprising at least 5 members, which may be monocyclic or polycyclic, fused or non-fused, optionally comprising at least one heteroatom chosen from N, O, S and P; wherein the aryloxy, heteroaryloxy, aryl and heteroaryl groups optionally bear at least one substituent chosen from halogen atoms, C$_{1-9}$ alkyl radicals, hydroxyl radicals, C$_{1-6}$ alkoxy radicals, amino radicals, mono- and di(C$_{1-6}$ alkyl)amino radicals, mono- and di(C$_{1-6}$ hydroxyalkyl) amino radicals, thio radicals, C$_{1-6}$ alkylthio radicals, C$_{1-6}$ thioalkyl radicals, (C$_{1-6}$ alkyl)carbonyl radicals, hydrogenocarbonyl radicals, hydroxycarbonyl radicals, (C$_{1-6}$ alkoxy)carbonyl radicals, nitro radicals, sulphonato radicals, tri(C$_{1-6}$ alkyl)ammonio radicals, imidazolyl radicals, pyridinyl radicals, and the corresponding protonated radicals;

and two adjacent substituents may together comprise the group —O—CH$_2$—O—;

with the proviso that at least one of the radicals R$^1$, R$^2$, R$^3$, and R$^4$ are not a hydrogen atom, or R$^1$ and R$^2$, R$^2$ and R$^3$ or R$^3$ and R$^4$ are together form the group —O—CH$_2$—O—; and at least one compound chosen from compounds comprising a primary or secondary amine functional group and compounds comprising an activated methylene functional group, wherein the ready-to-use dyeing composition is prepared at the time of use.

15. A multicomponent ready-to-use dyeing composition comprising, in a cosmetically acceptable medium, at least one first component comprising a composition comprising at least one ninhydrin compound of formula (I):

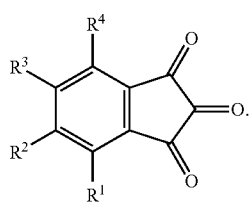

wherein

R$^1$, R$^2$, R$^3$ and R$^4$, which may be identical or different, are chosen from hydrogen atoms; carboxy(C$_{1-6}$ alkyl)radicals; (C$_{1-6}$ alkyl)carboxy(C$_{1-6}$ alkyl) radicals; 6-membered aryloxy radicals; 5-membered heteroaryloxy radicals comprising at least one heteroatom chosen from N, O, S and P; aryl radicals comprising at least 5 members, which may be monocyclic or polycyclic, fused or non-fused, optionally comprising at least one heteroatom chosen from N, O, S and P; wherein the aryloxy, heteroaryloxy, aryl and heteroaryl groups optionally bear at least one substituent chosen from halogen atoms, C$_{1-9}$ alkyl radicals, hydroxyl radicals, C$_{1-6}$ alkoxy radicals, amino radicals, mono- and di(C$_{1-6}$ alkyl)amino radicals, mono- and di(C$_{1-6}$ hydroxyalkyl) amino radicals, thio radicals, C$_{1-6}$ alkylthio radicals, C$_{1-6}$ thioalkyl radicals, (C$_{1-6}$ alkyl)carbonyl radicals, hydrogenocarbonyl radicals, hydroxycarbonyl radicals, (C$_{1-6}$ alkoxy)carbonyl radicals, nitro radicals, sulphonato radicals, tri(C$_{1-6}$ alkyl)ammonio radicals, imidazolyl radicals, pyridinyl radicals, and the corresponding protonated radicals;

and two adjacent substituents may together comprise the group —O—CH$_2$—O—;

with the proviso that at least one of the radicals R$^1$, R$^2$, R$^3$, and R$^4$ are not a hydrogen atom, or R$^1$ and R$^2$, R$^2$ and R$^3$ or R$^3$ and R$^4$ are together form the group —O—CH$_2$—O—, and at least one second component comprising at least one composition comprising at least one compound chosen from compounds comprising a primary or secondary amine functional group and compounds comprising an activated methylene functional group.

16. A multicompartment kit for dyeing keratin fibers comprising, at least one first compartment comprising at least one first component comprising at least one ninhydrin compound of formula (I):

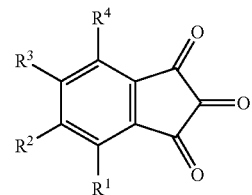

wherein

R$^1$, R$^2$, R$^3$ and R$^4$, which may be identical or different, are chosen from hydrogen atoms; carboxy(C$_{1-6}$ alkyl)radicals; (C$_{1-6}$ alkyl)carboxy(C$_{1-6}$ alkyl) radicals; 6-membered aryloxy radicals; 5-membered heteroaryloxy radicals comprising at least one heteroatom chosen from N, O, S and P; aryl radicals comprising at least 5 members, which may be monocyclic or polycyclic, fused or non-fused, optionally comprising at least one heteroatom chosen from N, O, S and P; wherein the aryloxy, heteroaryloxy, aryl and heteroaryl groups optionally bear at least one substituent chosen from halogen atoms, C$_{1-9}$ alkyl radicals, hydroxyl radicals, C$_{1-6}$ alkoxy radicals, amino radicals, mono- and di(C$_{1-6}$ alkyl)amino radicals, mono- and di(C$_{1-6}$ hydroxyalkyl) amino radicals, thio radicals, C$_{1-6}$ alkylthio radicals, C$_{1-6}$ thioalkyl radicals, (C$_{1-6}$ alkyl)carbonyl radicals, hydrogenocarbonyl radicals, hydroxycarbonyl radicals, (C$_{1-6}$ alkoxy)carbonyl radicals, nitro radicals, sulphonato radicals, tri(C$_{1-6}$ alkyl)ammonio radicals, imidazolyl radicals, pyridinyl radicals, and the corresponding protonated radicals;

and two adjacent substituents may together comprise the group —O—CH$_2$—O—;

with the proviso that at least one of the radicals R$^1$, R$^2$, R$^3$, and R$^4$ is not a hydrogen atom, or R$^1$ and R$^2$, R$^2$ and R$^3$ or R$^3$ and R$^4$ are together form the group —O—CH$_2$—O—, and at least one second compartment comprising at least one second component comprising at least one compound chosen from compounds comprising a primary or secondary amine functional group and compounds comprising an activated methylene functional group.

17. A process of dyeing hair comprising the application, to the hair, of a multi-component ready-to-use dyeing composition according to claim 15, waiting a sufficient leave-in time to allow a desired color to be obtained, and then rinsing and washing the hair.

18. The process for dyeing hair according to claim 17, further comprising heating hair impregnated with the hair dyeing composition to a temperature of less than or equal to 80° C.

19. The process for dyeing hair according to claim 18, further comprising heating hair impregnated with the hair dyeing composition to a temperature of less than or equal to 60° C.

20. A process for dyeing hair according to claim 15, comprising the successive application, to the hair, in any order, of the at least one first component and the at least one second component.

21. The process for dyeing hair according to claim 20, further comprising an intermediate rinsing step between the application of the at least one first or second component and the application of the at least one first or second component.

22. The process for dyeing hair according to claims 20, comprising heating the hair impregnated with either the at least one first or at least one second component to a temperature of less than or equal to 80° C. before the application of the remaining at least one first or at least one second component.

23. The process according to claim 22, wherein the impregnated hair is heated to a temperature of less than or equal to 60° C.

* * * * *

UNITED STATES PATENT AND TRADEMARK OFFICE
CERTIFICATE OF CORRECTION

| | |
|---|---|
| PATENT NO. | : 7,179,306 B2 |
| APPLICATION NO. | : 10/898370 |
| DATED | : February 20, 2007 |
| INVENTOR(S) | : Grégory Plos et al. |

It is certified that error appears in the above-identified patent and that said Letters Patent is hereby corrected as shown below:

In claim 1, column 14, line 5, delete "are".

In claim 6, column 14, lines 50-51, "5-(2-hydroxyethylamino)4-methoxy-2-methylphenol," should read --5-(2-hydroxyethylamino)-4-methoxy-2-methylphenol,--.

In claim 6, column 15, line 33, "O-$(CH_2)_p$,NH and NH-$(CH_2)_p$-O" should read --O-$(CH_2)_p$NH and NH-$(CH_2)_p$,-O--.

In claim 12, column 16, line 3, "where in" should read --wherein--.

In claim 13, column 16, line 50, delete "are".

In claim 14, column 17, line 27, delete "are".

In claim 15, column 18, line 11, delete "are".

In claim 16, column 18, line 61, delete "are".

In claim 22, column 20, line 5, "claims" should read --claim--.

Signed and Sealed this

First Day of May, 2007

JON W. DUDAS
*Director of the United States Patent and Trademark Office*